United States Patent [19]
Liebert et al.

[11] Patent Number: 5,256,154
[45] Date of Patent: Oct. 26, 1993

[54] PRE-FILLED PLASTIC SYRINGES AND CONTAINERS AND METHOD OF TERMINAL STERILIZATION THEREOF

[75] Inventors: Richard T. Liebert, Ballston Spa; Neil H. Brown, Nassau; Randy E. Armbruster, Rochester, all of N.Y.; Thomas M. Pack, Lower Gwynedd, Pa.

[73] Assignee: Sterling Winthrop, Inc., New York, N.Y.

[21] Appl. No.: 829,106

[22] Filed: Jan. 31, 1992

[51] Int. Cl.⁵ .............................................. A61M 5/32
[52] U.S. Cl. ................................................ 604/199
[58] Field of Search ............... 604/199, 110, 218, 221, 604/222, 236, 238, 232

[56] References Cited

U.S. PATENT DOCUMENTS

| | | |
|---|---|---|
| 3,270,483 | 6/1966 | Smoyer et al. |
| 3,468,471 | 9/1969 | Linder |
| 3,705,582 | 12/1974 | Stumpf et al. |
| 3,902,491 | 9/1975 | Lajus .................. 604/221 |
| 4,406,861 | 9/1983 | Beauvais et al. |
| 4,457,327 | 7/1984 | Pepper |
| 4,718,463 | 1/1988 | Jurgens et al. |
| 5,062,839 | 11/1991 | Seghi .................. 604/110 |

FOREIGN PATENT DOCUMENTS 14330 of 1929 Australia ............................. 604/236

Primary Examiner—C. Fred Rosenbaum
Assistant Examiner—Manuel Mendez
Attorney, Agent, or Firm—Imre (Jim) Balogh; Arthur Rosenstein

[57] ABSTRACT

Disclosed is a pre-filled plastic syringe containing a liquid product for terminal sterilization comprising: a syringe barrel equipped with a one-way valve and a slidable plunger to equalize pressure differentials; a filter engaging the one way valve to prevent backward migration of viruses and bacteria; an end cap covering the open end of the barrel to maintain sterility; and an end cap restraining device to prevent plunger blow-out.

7 Claims, 6 Drawing Sheets

PRE-FILLED PLASTIC SYRINGES AND CONTAINERS AND METHOD OF TERMINAL STERILIZATION THEREOF

BACKGROUND OF THE INVENTION

1. Field of the Invention

The present invention relates generally to pre-filled plastic syringes and containers containing liquid pharmaceutical, biological or veterinary products therein and to a process for terminal sterilization thereof. More particularly, the invention relates to pre-filled plastic syringes containing liquid contrast media for parenteral administration and to a process for terminal sterilization thereof.

2. Reported Developments

The prior art discloses processes, apparatus and containers for the sterilization of products and medical devices used in the health and medical fields where sterilization is an absolute requirement. Generally speaking, such sterilization may be accomplished by sterilizing the containers and contents separately, followed by placing the contents into the containers and hermetically sealing the same for use at a later time. However, such processes carry the risk of contamination and introduction of pyrogens during transfer of the products into their containers. The preferred method of achieving sterile finished products or ready to use sterile medical devices is through the use of terminal sterilization by autoclaving.

In the process of terminal sterilization, the pre-filled containers/packages are placed in an autoclave and are subjected to operational cycles which include: creating a vacuum in the autoclave by evacuating air therefrom; introducing steam in the autoclave so that the temperature therein reaches about 270° F.; maintaining the temperature for a time sufficient to sterilize the content of the autoclave; vacuum drying for about one hour while maintaining the temperature around 270° F.; and cooling the autoclave and removing the containers therefrom. Typical containers containing parenteral formulations, such as glass ampules, stoppered vials and bottles are able to withstand the pressure differentials between the containers and the autoclave chamber created by the operational cycles of the sterilization process. However, pre-filled syringes and cartridges made of plastic do not tolerate significant pressure differentials when the internal pressure is greater than the external; such pressure differential results in deformation and warping of the plastic walls that will occur either during the heating phase or the cooling phase of the autoclave cycle.

As a consequence, provision must be made to prevent deformation of container walls which may cause leakage of content through separation of seal of the container and contamination of the product from the environment during the process of terminal sterilization and subsequent shelf-life. The problem associated with pressure differential has been overcome by a method disclosed in U.S. Pat. No. 4,718,463, which provides for maintaining a pressure on the outside surfaces of the syringe at least equal to the pressure inside the syringe during autoclaving, i.e. by maintaining an autoclave overpressure.

The present invention provides a method for terminal steam sterilization of pre-filled plastic containers and syringes without the necessity of autoclave overpressure.

The present invention also provides pre-filled plastic containers and syringes that are steam sterilizable essentially without risk of deformation, leakage of content and contamination.

Other objects, features and advantages of the present invention will be apparent from the description that follows.

SUMMARY OF THE INVENTION

In accordance with the invention, a pre-filled syringe for autoclaving a sterilizable material contained therein is provided comprising:

a barrel having a distal end terminating in a nozzle and an open or proximal end having a flange for connecting an end cap and an end cap restraining device thereto;

a one-way valve or check valve, hereinafter "one-way valve", removably mounted onto said nozzle to release pressure generated in the syringe during autoclaving;

a slidable plunger in the barrel located in the proximity of the open end thereof to retain the sterilizable material and to slide toward the proximal end or distal end of the barrel in response to pressure differentials inside the barrel and the autoclave chamber;

an end cap having a base and a compressible bulb connected to the flange of the proximal end of the barrel to maintain sterility during the sliding movement of the plunger; and an end cap restraining device to prevent expulsion of plunger and end cap as a result of excessive pressure in the syringe.

In a preferred embodiment a viral/microbial filter hereinafter "filter", is mounted on the one-way valve to prevent backward migration of viruses and bacteria when the one-way valve opens in response to increased pressure inside the syringe.

In another aspect the present invention provides a method for sterilizing materials, especially liquid pharmaceutical products, such as liquid contrast media for diagnostic examination, in a syringe wherein the syringe comprises:

a barrel having a distal end terminating in a nozzle and an open or proximal end having a flange for connecting an end cap and an end cap restraining device thereto;

a one-way valve removably mounted onto said nozzle to release pressure generated in the syringe during autoclaving;

a slidable plunger in the barrel located in the proximity of the open end thereof to retain the sterilizable material and to slide toward the proximal end or distal end of the barrel in response to pressure differentials inside the barrel and the autoclave chamber;

an end cap having a base and a compressible bulb connected to the flange of the proximal end of the barrel to maintain sterility during the sliding movement of the plunger; and an end cap restraining device to prevent expulsion of plunger and end cap as a result of excessive pressure in the syringe, said method comprising the steps of:

mounting the one-way valve onto the nozzle of the barrel;

positioning the barrel with its open end up;

filling the barrel with the liquid material to be sterilized;

inserting the plunger into the barrel;
closing the open end of the barrel by engaging the flange of the end cap with the flange of the barrel;
closing the barrel at its proximal end by engaging the end cap restraining device with the flange of the barrel; and
autoclaving the pre-filled assembled syringe to sterilize the liquid material therein.

In a method utilizing the preferred embodiment of the invention, the filter is engaged onto the one-way valve before filling the barrel with the liquid material. Alternatively, the one-way valve and filter may be pre-assembled before mounting the one-way valve onto the nozzle of the barrel. The syringe is then loaded into an autoclave with its distal end up. Upon heating, the pressure increases within the syringe as temperature increases. When the pressure differential between the inside of the syringe and the autoclave chamber exceeds the activation or opening pressure of the check valve, excess pressure within the syringe is vented until the valve activation pressure is again reached. Acting concurrently with the one-way valve is the pressure equalizing feature of the plunger. If the pressure differential between the inside of the syringe and the autoclave chamber is greater than the resistance between the plunger and barrel, the plunger will move either toward the distal end or the proximal end of the barrel depending on the pressure inside or outside the syringe. If the pressure inside the syringe is greater than the resistance offered by the fit of the plunger in the barrel but less than the valve activation pressure of the one-way valve, the plunger will slide back toward the proximal end of the barrel and stop when it reaches the end cap on the proximal end of the barrel. Conversely, if the pressure outside the syringe, i.e. in the autoclave chamber, is greater than the pressure within the syringe and this pressure differential is greater than the resistance between the plunger and barrel, the plunger will slide toward the distal end of the barrel. During the cooling cycle of the autoclave process the plunger will move toward the distal end of the barrel, since the contraction of the liquid and gases contained in the syringe generates a vacuum thereby greatly reducing the pressure within the syringe. This negative pressure or vacuum in the barrel is partially relieved by the plunger movement toward the distal end of the barrel. During the cooling cycle the check valve or one-way valve is closed by the outside or autoclave pressure which is greater than the check valve activation pressure. As the plunger slides toward the distal end of the barrel, sterility inside the barrel is maintained through the function of the end cap fitted over the proximal end of the barrel. Additionally, the end cap, through its compressible bulb, functions to slow the movement of the plunger toward the proximal end of the barrel when the pressure increases inside the barrel. During the sterilization process the end cap restraining device insures against blow-out of the plunger and consequent failure of sterility. Upon completion of the autoclaving process the syringe is stored for future use of its content. At the point of use the one-way valve, the end cap restraining device and the end cap are removed and the syringe is then ready for use the conventional way.

DESCRIPTION OF THE PREFERRED EMBODIMENTS

Figure 1:
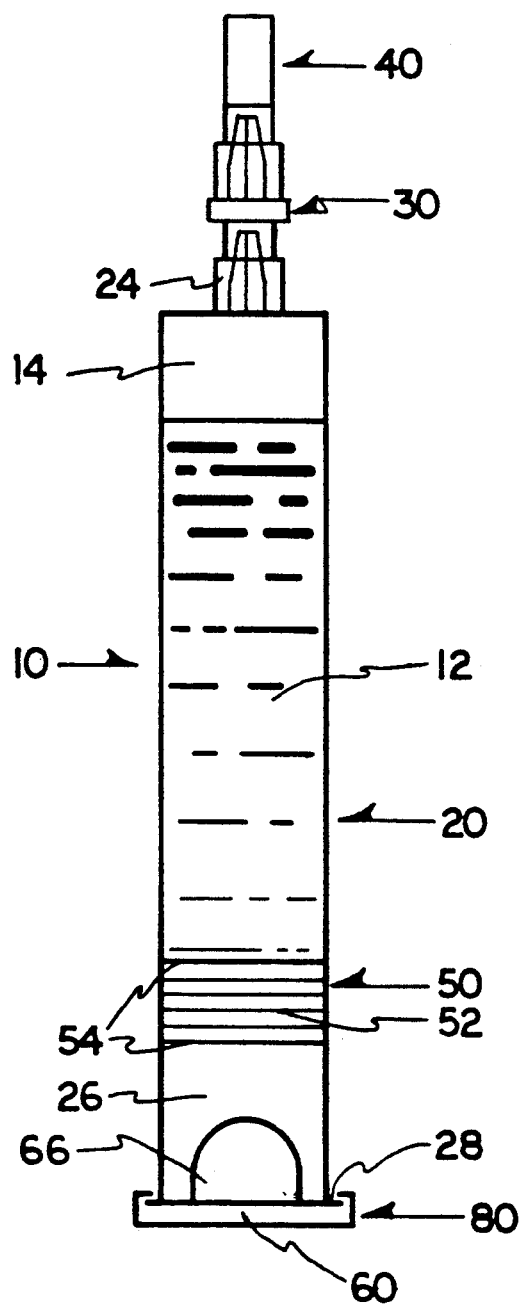
FIG. 1 is a sectional view of a pre-filled plastic syringe in accordance with the invention.
Figure 2:
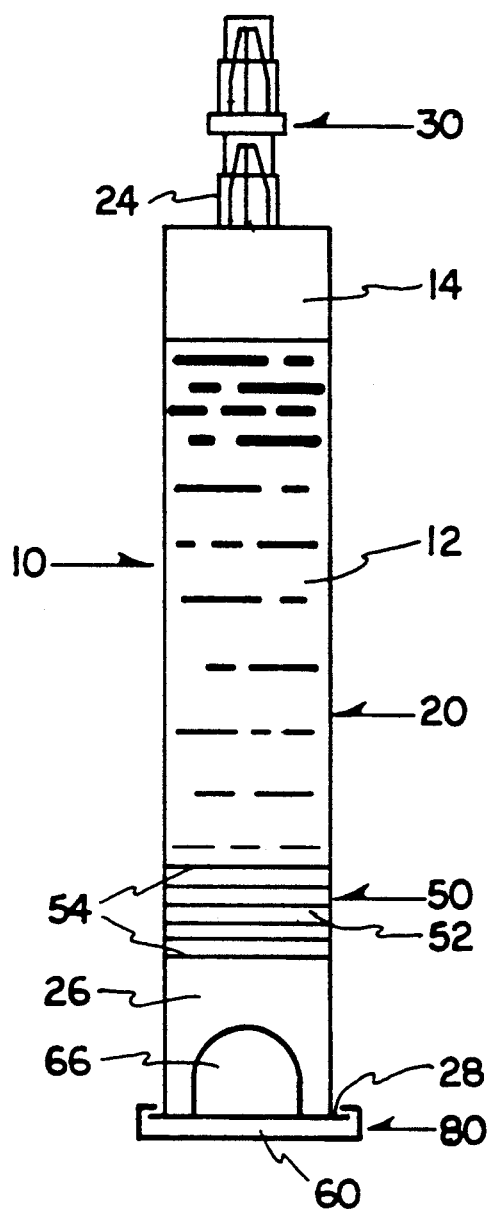
FIG. 2 is a sectional view of another embodiment of the pre-filled plastic syringe in accordance with the invention.

As shown in FIGS. 1 and 2, a pre-filled plastic syringe indicated generally by number 10, according to the invention comprises: a syringe barrel 20 having a nozzle 24 at the distal end and an open or proximal end 26. The barrel comprises a circular, outwardly extending flange 28 which is adapted to receive an end cap. Nozzle 24 is closed by a removably mounted one-way valve 30, and in the FIG. 1 embodiment the one-way valve 30 is also equipped with a filter 40. The barrel 20 contains a slidable plunger or piston 50 which is positioned close to the open or proximal end 26 of the barrel. Also removably mounted on the open end 26 of the barrel is an end cap 60, shown in detail in FIG. 6 and an end cap restraining device 80 to prevent expulsion of the plunger 50 and the end cap 60.

Figure 3:
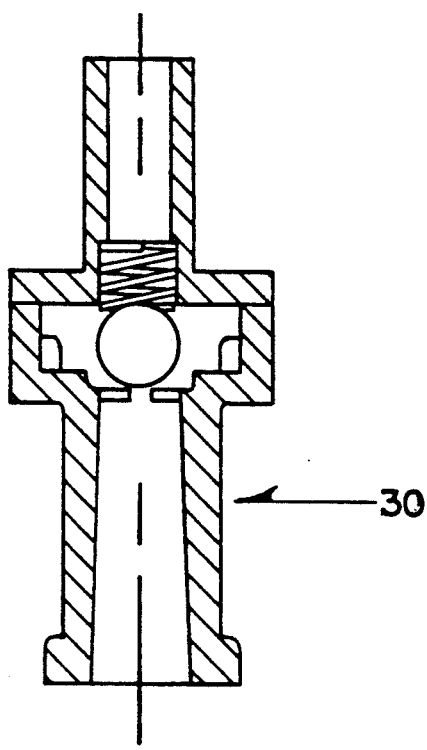
FIG. 3 is a sectional view of a one-way valve used in the embodiments of the invention shown in FIG. 1 and FIG. 2.
Figure 4:
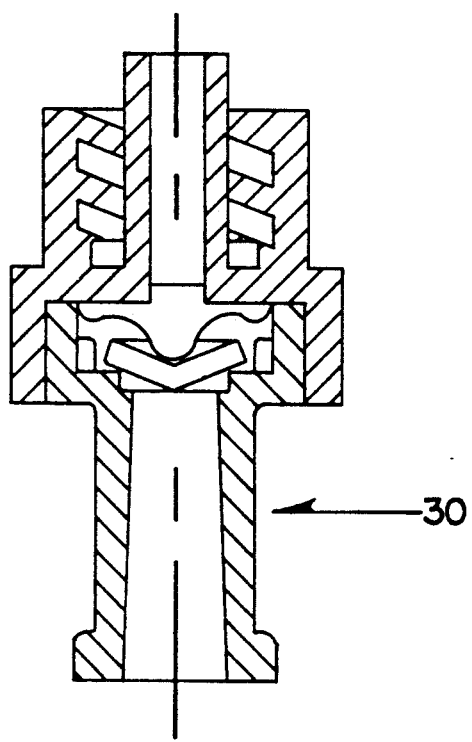
FIG. 4 is a sectional view of another type of one-way valve used in the embodiments of the invention shown in FIG. 1 and FIG. 2.

Turning now specifically to the component parts of the embodiments shown in FIGS. 1 and 2, syringe barrel 20 is made of polymeric materials such as polypropylene or co-polymers of polyethylene and polypropylene by techniques known in the art, such as by injection molding. One-way valve 30 may be any high pressure check valve allowing fluid release or flow of fluid one way and preventing backflow from the other direction designed for use in the medical field, such as shown in FIGS. 3 and 4. Such one-way valves are well-known in the prior art, for example, in U.S. Pat. No. 4,535,820, which is incorporated by reference herein.

Figure 5:
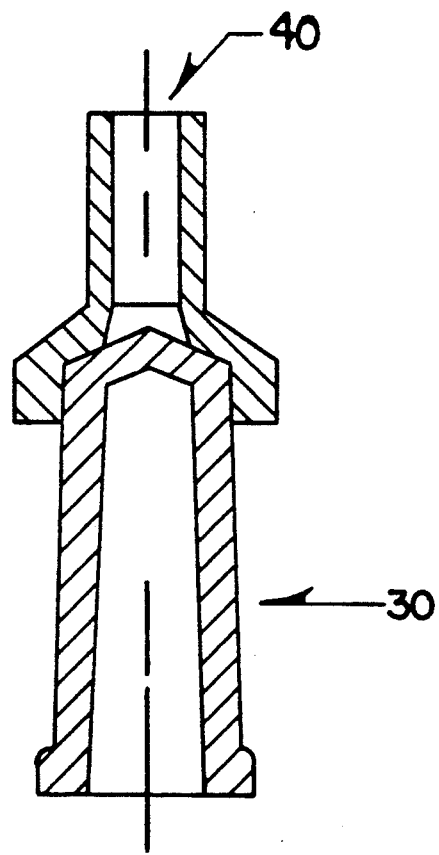
FIG. 5 is a sectional view of a filter and one-way valve combination used in the embodiment of the invention shown in FIG. 1.

A viral/microbial filter cartridge 40 is preferably used with the device of the present invention. Its function is to prevent backward migration of viruses and bacteria during the time when the one-way valve 30 is in the open position. Viral/microbial filters are commercially available and are adapted to hermetically cover one-way valve 30, such as shown in FIG. 5.

Plunger 50 of the pre-filled syringe 10 comprises an elastomeric base member 52 which is inert to the liquid contained in the syringe, or is coated with an inert polymeric material 54, such as TEFLON. The plunger must fit tightly in the barrel 20 of the syringe and must be liquid-tight so that the liquid chemical or medicament will not bypass the plunger when positive or negative pressure inside the barrel 20 forces the plunger to slide either towards the proximal end or distal end of the barrel.

Figure 6:
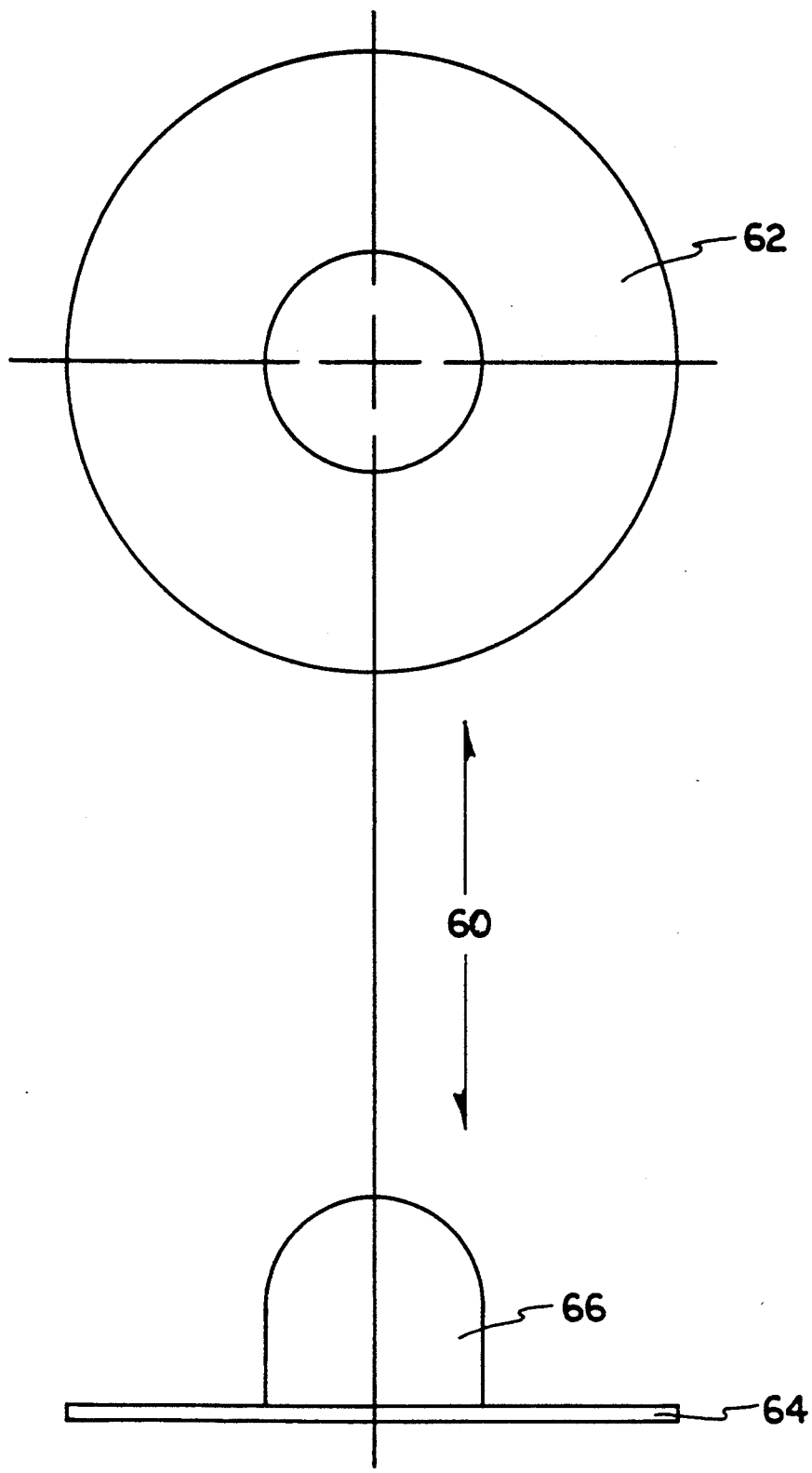
FIG. 6 is a sectional view of an end cap.
Figure 7:
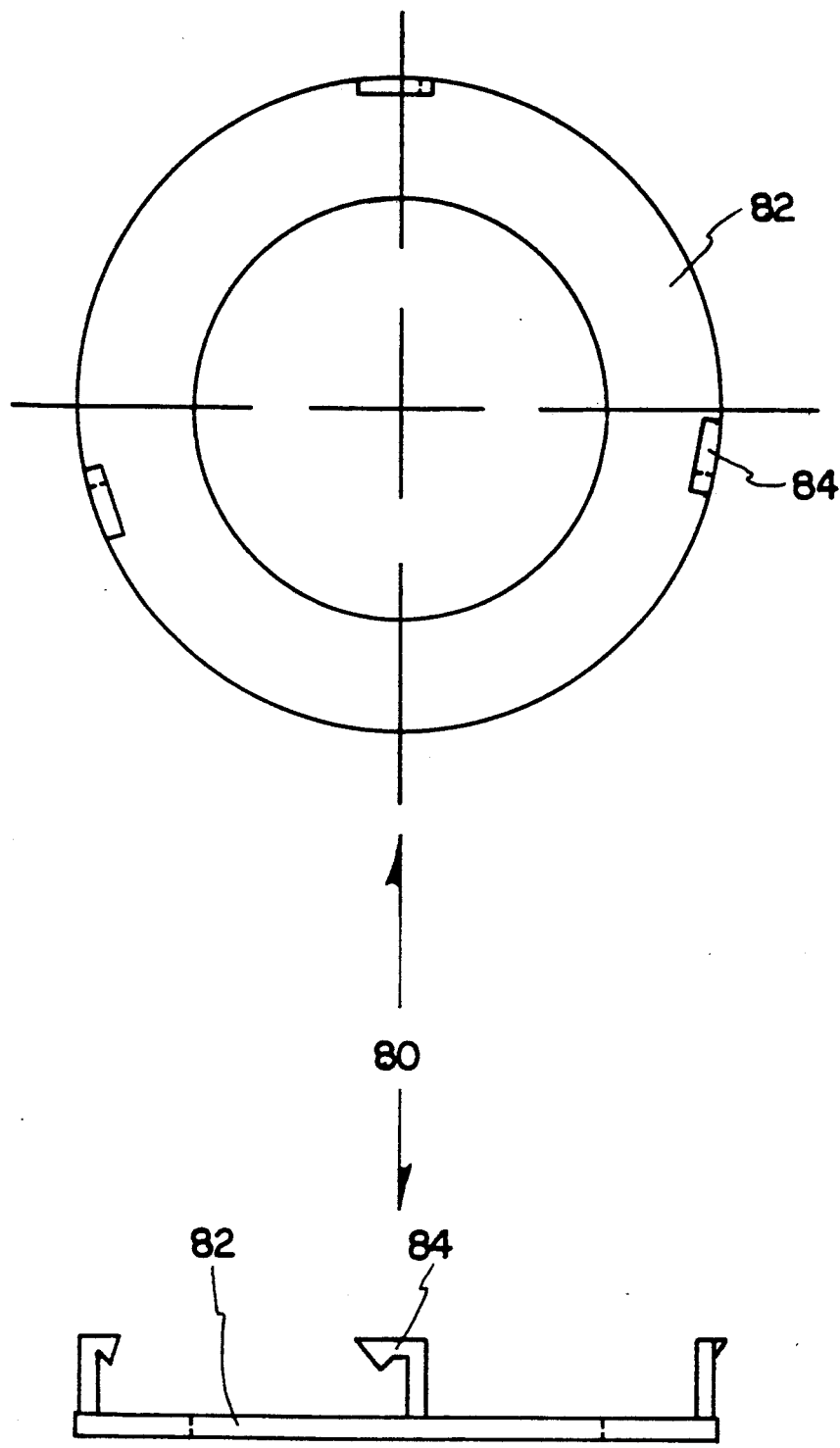
FIG. 7 is a sectional view of an end cap restraining device.

End cap 60, as shown in FIG. 6, is adapted to removably engage flange 28 of barrel 20, and comprises: a semi-rigid base 62 having flange 64 to engage flange 28 of the barrel in a mating relationship to seal the proximal end 26 of the barrel 20; and a bulb portion 66 made of highly elastomeric materials which compresses or expands in response to the position of the plunger. The function of the end cap 60 is to maintain the sterile integrity of the syringe during the sliding movement of the plunger in response to the internal positive or negative pressure in the barrel.

End cap restraining device 80 comprises a rigid circular-shaped body 82 adapted to engage flange 28 of the barrel by hook-shaped means 84 to insure retention of the plunger 50 and end cap 60 when overpressure develops inside the syringe during the sterilization cycle.

The end cap and end cap restraining device are individually manufactured by conventional plastic-forming processes using suitable polymeric materials well-known in the art.

In practicing the method of the present invention, prior to sterilizing the pre-filled syringes, the component parts are first cleaned and inspected according to accepted manufacturing practices. Next, one-way valve 30 is mounted onto nozzle 24 of the barrel 20 and barrel 20 is positioned with its proximal end 26 positioned upward; next, the barrel is filled with the sterilizable liquid 12 and plunger 50 is inserted followed by positioning end cap 60 onto the barrel 20 by engaging flange 28 of the barrel with flange 64 of the end cap in a mating relationship; and finally closing the proximal end of the barrel 20 with the end cap restraining device 80 by engaging flange 28 of the barrel 20 by hook-shaped means 84 and loading the pre-filled assembled syringe with its distal end up into an autoclave. Upon adding heated steam/air to the autoclave, the pressure increases within the syringe. When the pressure differential between the inside of the syringe 10 and the autoclave chamber exceeds the activation or opening pressure of the check valve 30, excess pressure within the syringe is vented until the pressure in the syringe reaches the pressure of the autoclave chamber.

Acting concurrently with one-way valve 30, the plunger 50 also acts to equalize pressure. If the pressure inside the syringe 10 is greater than the resistance offered by the fit of the plunger 50 in the barrel but less than the activation pressure of the one-way valve 30, plunger 50 will slide toward the proximal end 26 of the barrel 20 and stop when it reaches end cap 60 and compresses bulb 66. Conversely, if the pressure in the autoclave chamber is greater than the pressure within the syringe 10, and the pressure differential is greater than the resistance between the plunger 50 and the barrel 20, the plunger will slide toward the distal end of the barrel 20.

During the heating and cooling cycle of the autoclave process, the bulb portion 66 of the end cap 60 compresses and expands in response to the sliding movement of the plunger 50 as a result of the positive pressure or vacuum created in the barrel 20.

End cap restraining device 80 insures against blowout of the plunger 50 when internal pressure forces the plunger toward the proximal end of the barrel 20.

While in the preferred embodiment, shown and described, the syringe comprises a flange for engagement of the end cap and end cap restraining device, other means for attachment may also be used, such as thread means or locking ears. In such cases the end cap and end cap restraining device will be adapted to engage said thread means or locking ears on the syringe.

While the invention has been described with respect to a syringe configuration which is the preferred embodiment, other configurations, such as plastic containers and vials may also be used in practicing the invention. It therefore is the intent that the invention encompass such plastic containers and vials since they fall within the scope and spirit of the invention.

What is claimed is:

1. A pre-filled plastic syringe for autoclaving a sterilizable material contained therein comprising:
    a barrel having a distal end terminating in a nozzle and a proximal end;
    a one-way valve removably mounted onto said nozzle;
    a slidable plunger in the barrel located in the proximity of the proximal end thereof;
    an end cap removably connected to the proximal end of the barrel; and
    an end cap restraining device removably mounted to the proximal end of the barrel over the end cap.

2. The pre-filled plastic syringe of claim 1 wherein:
    said proximal end of the barrel comprises a flange; and said end cap having a base with a flange thereon to removably engage the flange of the barrel to maintain sterility during the sliding movement of the plunger.

3. The pre-filled plastic syringe of claim 2 wherein said end cap further comprises a compressible bulb integral with the base of the end cap and extending into the barrel toward the slidable plunger and adapted to be compressed by the slidable plunger when pressure increases inside the barrel during autoclaving.

4. A pre-filled plastic syringe for autoclaving a sterilizable material contained therein comprising:
    a barrel having a distal end terminating in a nozzle and a proximal end having a flange;
    a one-way valve removably mounted onto said nozzle for the release of pressure generated in the syringe during autoclaving;
    a slidable plunger in the barrel located in the proximity of the proximal end thereof to retain said sterilizable material and to slide toward the proximal end or distal end of the barrel in response to pressure differentials inside the barrel and the autocalve chamber;
    an end cap having a base with a flange and a compressible bulb thereon sealingly connected to said flange on the proximal end of said barrel to maintain sterility during the sliding movement of the plunger, said compressible bulb integral with the base of the end cap and extending into the barrel toward the slidable plunger and adapted to be compressed by the slidable plunger when pressure increases inside the barrel during autoclaving; and
    an end cap restraining device having hook-shaped means to engage the flange on the proximal end of the barrel to prevent expulsion of the plunger.

5. The pre-filled plastic syringe of claim 4 wherein said end cap comprises: a semi-rigid base having a flange to engage the flange at the proximal end of the barrel in a mating relationship and hermetically seal said proximal end of the barrel; and
    a compressible bulb portion of a highly elastomeric material extending into said barrel that compresses or expands in response to the pressure of the plunger exerted on said bulb portion.

6. A method of terminally sterilizing a material in a syringe for chemical/pharmaceutical use, said syringe comprising:
    a barrel having a distal end terminating in a nozzle and proximal end having a flange;

a one-way valve removably mounted onto said nozzle for the release of pressure generated in the syringe during autoclaving;

a slidable plunger in the barrel located in the proximity of the proximal end thereof to retain said sterilizable material and to slide toward the proximal end or distal end of the barrel in response to pressure differentials inside the barrel and the autoclave chamber;

an end cap having a base with a flange and a compressible bulb thereon sealingly connected to said flange on the proximal end of said barrel to maintain sterility during the sliding movement of the plunger; and an end cap restraining device having hook-shaped means to engage the flange on the proximal end of the barrel to prevent expulsion of the plunger, said method comprising the steps of:

mounting the one-way valve onto the nozzle of the barrel; positioning the barrel with its proximal end up;

filling the barrel with the liquid material to be sterilized; inserting the plunger into the barrel; closing the proximal end of the barrel by engaging the flange of the end cap with the flange of the barrel; securing retention of the end cap in the barrel by closing the proximal end thereof with the end cap restraining device; and autoclaving the pre-filled assembled syringe to sterilize the liquid material therein.

7. The method of claim 6 wherein said end cap comprises: a semi-rigid base having a flange to engage said flange at the proximal end of the barrel in a mating relationship and hermetically sealing said barrel; and a compressible bulb portion of a highly elastomeric material extending into said barrel that compresses or expands in response to the pressure of the plunger exerted on said bulb portion.

* * * * *